United States Patent [19]
DeVries

[11] Patent Number: 6,096,893
[45] Date of Patent: Aug. 1, 2000

[54] PROCESS AND INTERMEDIATES FOR 3-HETEROARYL-4(3H) QUINAZOLINES

[75] Inventor: Keith M. DeVries, Chester, Conn.

[73] Assignee: Pfizer Inc., New York, N.Y.

[21] Appl. No.: 09/375,215

[22] Filed: Aug. 16, 1999

Related U.S. Application Data

[60] Provisional application No. 60/097,405, Aug. 21, 1998.
[51] Int. Cl.$^7$ ............... C07D 211/70; C07D 211/82; C07D 213/46
[52] U.S. Cl. ........................... 546/328
[58] Field of Search ................... 546/328

[56] References Cited

FOREIGN PATENT DOCUMENTS

WO93/20053  10/1993  Japan .
WO9532198   11/1995  WIPO ............ C07D 403/14

OTHER PUBLICATIONS

CAS printout for WO 93/20053, Oct. 1993.

*Tetrahedron Letters*, vol. 37, No. 15, pp. 2537–2540, 1996, Cai, et al, "A Study of the Lithiation of 2,6–Dibromopyridine with Butyllithium, and its Application to Synthesis of L–739,010".

*Inorganic Chemistry*, vol. 10, No. 11, pp. 2472–2478, 1971, Parks, et al, "Three–Dimensional Macrocyclic Encapsulation Reactions. II.$^1$ Synthesis and Properties of Nonoctahedral Clathro Chelates Derived from Tris(2–aldoximo–6–pyridyl)phosphine and Boron Trifluoride or Tetrafluoroborate".

*J. Org. Chem.* 1997, 62, 8237–8239, Peterson, et al, "Efficient Preparation of 2–Bromo–6–lithiopyridine via Lithium–Bromine Exchange in Dichloromethane".

*Primary Examiner*—Mukund J. Shah
*Assistant Examiner*—H. L.
*Attorney, Agent, or Firm*—Peter C. Richardson; Gregg C. Benson; Mervin E. Brokke

[57] ABSTRACT

A new pyridine carbaldehyde is useful for the synthesis of compounds which are effective for treating neurodegeneration conditions and CNS trauma.

2 Claims, No Drawings

PROCESS AND INTERMEDIATES FOR 3-HETEROARYL-4(3H) QUINAZOLINES

This application claims benefit of provisional application Ser. No. 60/097,405 filed Aug. 21, 1998.

FIELD OF THE INVENTION

This invention relates to a novel pyridine carbaldehyde and process for synthesis of this aldehyde which is a useful intermediate for the preparation of 3-heteroaryl-4(3H)-quinazolinones which are effective for the treatment of neurodegenerative diseases and CNS trauma related conditions.

BACKGROUND OF THE INVENTION

PCT/IB98/00151 incorporated herein by reference, describes the synthesis and biological activity of atropisomers of 3-heteroaryl-4(3H)-quinazolines.

Atropisomers are isomeric compounds that are chiral, i.e. each isomer is not superimposable on its mirror image and the isomers, once separated, rotate polarized light in equal amounts but opposite directions. Atropisomers are distinguished from enantiomers in that atropisomers do not possess a single asymmetric atom. Atropisomers are conformational isomers which occur when rotation about a single bond in the molecule is prevented or greatly slowed as a result of steric interactions with other parts of the molecule and the substitutents at both ends of the single bond are unsymmetrical. A detailed account of atropisomers can be found in Jerry March, *Advanced Organic Chemistry*, 101–102 (4th ed. 1992) and in Oki, *Top. Stereochem.*, 14, 1–81 (1983).

The compounds of PC9803 provide the first evidence that atropisomers of quinazolinones are seperable and that the separated isomers possess differential AMPA receptor antagonist activity. (AMPA receptors are a subspecies of the glutamate receptors, identified by their ability to bind α-amino-3-hydroxy-5-methyl-4-isoxazolepropionic acid (AMPA), that are post synaptic neurotransmitter receptors for excitatory amino acids.) Colebrook et al., *Can. J. Chem.*, 53, 3431–4, (1975) observed hindered rotation about aryl C—N bonds in quinazolinones but did not separate or suggest that the rotational isomers could be separated. U.S. patent application Ser. No. 60/017,738 filed May 15, 1996 and entitled "*Novel 2,3-Disubstituted -4-(3H)-Quinazolinones*" and U.S. patent application 60/017,737 filed May 15, 1996 and entitled "Novel 2,3-Disubstituted-(5,6)-Heteroarvlfused-Pyramidin-4-ones," both applications herein incorporated by reference in their entirety, refer to racemic quinazolinones and pyrimidones. The inventors of PCT/IB98/00151 discovered that one quinazolinone isomer, defined by the spatial positions of the substituents arising out of steric interactions, possesses all of the AMPA receptor antagonist activity.

The role of excitatory amino acids, such as glutamic acid and aspartic acid, as the predominant mediators of excitatory synaptic trasnmission of the central nervous system has been well established. Watkins & Evans, *Ann. Rev. Pharmacol. Toxicol.*, 21,165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified in to two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-proopionic acid (AMPA), and Kainic acid (KA). The second general type is the G-protein or second messenger-linked "metabotropic" excitatory amino acid receptor. This second type, when activated by the agonists quisqualate, ibotenate, or trans-1-aminocuclopentane-1 ,3-dicarboxylic acid, leads to enhanced phosphoinosoitide hydrolysis in the postsynaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by a way of a mechanism known as excitotoxicity. The process has been suggested to mediate neuronal degeneration in a variety of conditions. The medical consequences of such neoronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to or resulting from cardiac bypass surgery and grafting, stroke, cerebral ischemia, spinal cord trauma, head trauma, Alzheimer's Disease, Huntington's Chorea, amyotrophic lateral sclerosis, epilepsy, Aids-induced dementia, perinatal hypoxia, hypoxia (such as conditions caused by strangulation, surgery, smoke inhalation, asphyxiation, drowing, choking, electrocution or drug or alcohol overdose), cardiac arrest, hypoglycemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic pain, convulsions, retinal neuropathy, tinnitus and tardive dyskinesia. The use of a neuroprotective agent, such as an AMPA receptor antagonist, is believed to be useful in treating these disorders and/or reducing the amount of neurological damage associated with these disorders. The excitatory amino acid receptor (EAA) antagonsts are also useful as analgesic agents.

Several studies have shown that AMPA receptor antagonist NBQX (2,3-dihydroxy-6-nitro-7-sulfamoylbenzo[f] quinoxoline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). These studies stronly suggest that the delayed neuronal degeneration in brain ischemia involves glutamate excitotoxicity mediated at least in art by AMPA receptor activation. Thus, AMPA receptor antagonists may prove useful as neuroprotective agents and improve the neurological outcome of cerebral ischemia in humans.

The preparation of 3-(2-chlorophenyl)-2-[2-(6-diethylaminomethylpyridin-2-yl)]-vinyl-6-fluoro-3H-quinazolin-4-one from 6-[2-[3-(2-chlorophenyl)-6-fluoro-4-oxo-3,4-dihydroquinazolin-2-yl]-vinyl]-pyridine-2-carbaldehyde and diethylamine in the presence of sodium triacetoxyborohydride is described in PCT/IB98/00151.

SUMMARY OF THE INVENTION

This invention provides the compound 6-diethylaminomethyl-pyridine-2-carbaldehyde.

This invention also provides a method for preparing 6-diethylaminomethyl pyrridine-2-carbaldehyde which comprises reacting 2-bromo-6-diethylaminomethyl pyridine with an organo lithium compound followed by dimethyl formamide.

In another aspect, this invention provides a method for preparing 2-bromo-6-diethylaminopyridine which comprises reacting 2,6-dibromopyridine with a molar amount of an organolithium compound followed by reaction with diethyl formamide and then with triacetoxyborohydride.

In another aspect, this invention provides a method for preparing 3-(2-chlorophenyl)-2-[2-(6-diethylaminomethylpyridin-2-yl)-vinyl]-6-fluoro-3H-quinozolin-4-one which comprises reacting 6-diethylaminomethyl-pyridine-2-carbaldehyde with 2-methyl-3-(2-chlorophenyl)-6-fluoro-3H-quinazolin-4-one in the presence of a Lewis acid.

DETAILED DESCRIPTION OF THE INVENTION

This invention provides the novel intermediate 6-diethylaminomethyl-pyridine-2-carbaldehyde (Formula I) which is useful for preparing 3-heteroaryl-4(3H) quinazolines. A specific method for using this compound is shown in the scheme below. All compounds shown in the scheme except compound I are known compounds in the chemical literature. This reaction scheme provides a novel and advantageous converging synthesis using the readily available 2,6-dibromo pyridine.

2-Bromo-6-diethylaminomethylpyridine is a known compound. See W095/32198, page 17. For the purposes of this invention, the compound was prepared as described in Example 1 below from 2,6-dibromopyridine by first forming the monolithium derivative followed by reduction of the intermediate amide. Triacetoxyborohydride is a preferred reducing agent.

Compound I is prepared from 2-bromo-6-dethylaminomethylpyridine by forming the lithium compound and subsequent reaction with dimethylformamide. A convenient method of isolation is formation of the bisulfate adduct of the aldehyde followed by treatment with base.

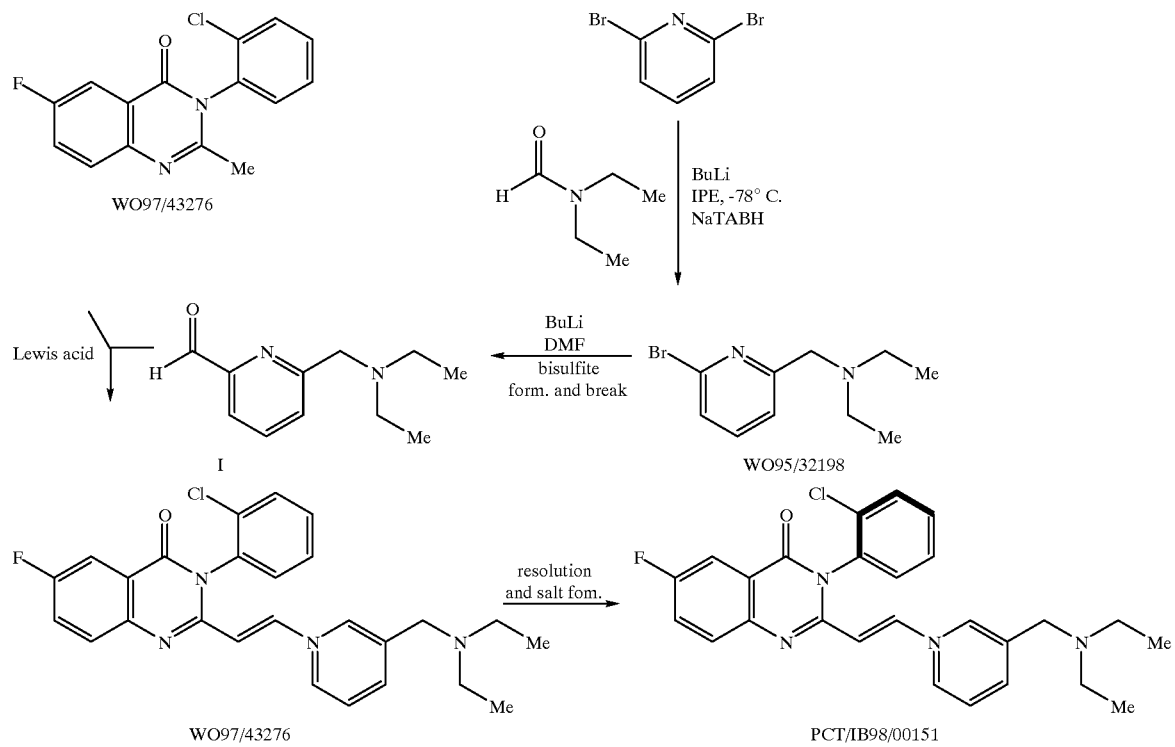

The compound of formula I is reacted with 2-methyl-3-(2-chlorophenyl)-6-fluoro-3H-quinozolin-4-one in the presence of a catalyst and a dehydrating agent in a suitable solvent to form 3-(2-chlorophenyl)-2-[2-(6-diethylaminomethyl pyridin-2-yl)-vinyl]-6-fluoro-3H-quinozolin-4-one. Suitable catalysts include zinc chloride, sodium acetate, aluminum chloride, tin chloride, or boron trifluoride etherate, preferably zinc chloride or sodium acetate. Suitable dehydrating agents include acetic anhydride, methane sulfonic anhydride, trifluoroacetic anhydride or propionic anhydride, preferably acetic anhydride. Suitable polar solvents include acetic acid, dioxane, dimethoxyethane or propionic acid. The termperature of the aforesaid reaction is from about 60° C. to about 100° C. for about 30 minutes to about 24 hours, preferably at about 100° C. for about 3 hours.

EXAMPLE 1

6-Diethylaminomethyl-pyridine-2-carbaldehyde

A slurry of 1500 gm of 2,6-dibromopyridine (6.33 mol, 1.0 equiv, MW 236.9) in 12 L (8 vol) of dry isopropyl ether (IPE) was held under a nitrogen sweep overnight in a 22 L round bottom. The slurry was then cooled to −60° C., and 2532 mL of n-BuLi (6.33 mmol, 2.5 M in hexanes, 1.0 eq) was added dropwise via addition funnel to maintain the temp at −60° C. The reaction slurry was then stirred for 30 minutes. (The slurry gradually thins.) TLC (50:50 hexane/methylene chloride) of an aliquot quenched into methanol showed only trace starting material.

Diethylformamide (775 mL, 6.96 mmol, 1.1 equiv, MW 101.15, d=0.908) was then added dropwise via addition funnel at a rate to keep the temperature at about 60° C. After stirring for 30 minutes, the slurry was warmed to −10° C.

Into a 50 L vessel was added 3 L of dry THF (2 vol) and 1313 mL of diethylamine (12.7 mol, 2.0 eq, MW 73.14, d=0.707). The 22 L reaction was transferred to buckets and then into the 50 L vessel. At this point, 1475 gm of sodium triacetoxyborohydride (6.96 mol, 1.1 eq, MW 211.94) was added. After warming to room temp, 725 mL of glacial acetic acid (12.7 mol, 2.0 equiv, MW 60, d=1.05) was added dropwise. The reaction was then monitored by TLC (95:5 methylene chloride/methanol) for disappearance of starting material.

The reaction slurry was quenched by the addition of 15 L of 1 N sodium hydroxide (10 vol) to the 50 L reactor. Beware of gas evolution. The final pH was about 10.5. The two phases were stirred for 60 minutes and then allowed to separate. The organic layer was washed with 3×1.5 L of water. The volatiles were stripped under vacuum to provide the product as an oil, which was held under vacuum overnight to provide 1,430 gm of the title compound as an oil (93% of theory, crude). This material was sufficient purity to carry into the next step as is.

$^1$H NMR (250 MHz, CDCl$_3$) δ7.46–7.48 (m, 2H), 7.26–7.32 (m, 1 H), 3.67 (s, 2H), 2.53 (q, J=7.2 Hz, 4H), 1.00 (t, J =7.2 Hz, 6H. MS (M+1)$^+$=243.

The product from the above step 2-bromo-6-diethylaminomethyl-pyridine (1,430 gm, MW 243.15, 5.88 mol, 1.0 equiv) was dissolved in 0.5 L of dry IPE and then transferred to an addition funnel. An additional 12 L (8 vol) of IPE was placed in a 22 L flask. The system was purged with a nitrogen bleed overnight.

The 22 L flask was cooled to −78° C. and 2470 mL of n-BuLi (2.5 M, 6.17 mol, 1.05 equiv) was added by cannula to the 22 L flask at <−60° C. The solution of step 2-bromo-6-diethylaminomethyl-pyridine was added dropwise to keep the temperature below −60° C. and stirred for an additional 30 minutes. TLC analysis of an aliquot quenced into methanol showed that the starting material was consumed.

478 mL of anhydrous DMF (MW 73.14, d=0.944, 6.17 mol, 1.05 equiv) was added at a rate to keep the temp at about −60° C. The solution was allowed to warm to −20° C. At this point the reaction was quenched into a 50 L reactor in the following manner. The reaction solution was slowly poured onto 980 ML (12 N, 11.8 mol, 2.0 equiv) of conc HCI diluted to 7.5 L (5 vol). The layers were separated, and the aqueous layer was extracted twice with 7.5 ethyl acetate (5 vol). The final pH is about 10.5. The combined organic layers were filtered to remove particulates and concentrated in vacuo.

The crude oil was treated with 917 gm of sodium bisulfite (MW 104, 8.8 mol, 1.5 equiv) in 15 L (10 vol) of water and 1.5 L (1 vol) of IPE. The biphasic mixture was stirred for one hour (pH about 6.5). The mixture was treated with 985 gm of sodium bicarbonate (MW 84, 11.8 mol, 2.0 equiv) to give a pH of about 8.0. Beware of gas evolution! The mixture was diluted with 7.5 (5 vol) of ethyl acetate and the layers separated. This was followed by two additional washes with 7.5 L of ethyl acetate.

The aqueous layer containing the bisulfite adduct was treated with 7.5 L (5 vol) of ethyl acetate followed by 412 gm (MW 40, 10.3 mol, 1.75 equiv) of sodium hydroxide dissolved in 1.5 L of water. The pH was adjusted to 11 if necessary. The organic layer was separated and the aqueous layer extracted twice more with 7.5 L (5 vol) of ethyl acetate. The volatiles were stripped in vacuo to provide 904 gm (80% of theory) of the title compound as an oil. This material was of sufficient purity to use directly in the synthesis of preparing 3-(2-chlorophenyl)-2-[2-(6-diethylaminomethylpyridin-2-yl)-vinyl]-6-fluoro-3H-quinozolin-4-one.

$^1$H NMR (250 MHz, CDCl$_3$) δ10.02 (s, 1H), 7.69–7.84 (m, 3H), 3.78 (s, 2H), 2.58 (q, J=7.2 Hz, 4H), 1.03 (t, J=7.2 Hz, 6H). MS (M+1)$^+$=193.

What is claimed is:

1. 6-Diethylaminomethyl-pyridine-2-carbaldehyde.
2. A method for preparing 6-diethylaminomethyl-pyridine-2-carbaldehyde which comrpises reacting 2-bromo-6-diethylaminomethyl-pyridine with an organo lithium compound followed by dimethyl formamide.

* * * * *